(12) United States Patent
Purdue et al.

(10) Patent No.: US 11,578,304 B2
(45) Date of Patent: Feb. 14, 2023

(54) HIGH DENSITY PRODUCTION OF BIOMASS AND OIL USING CRUDE GLYCEROL

(71) Applicant: MARA RENEWABLES CORPORATION, Dartmouth (CA)

(72) Inventors: Laura Purdue, Halifax (CA); Michael Milway, Dartmouth (CA); Kevin Berryman, Dartmouth (CA); Mercia Valentine, Eastern Passage (CA); Zhiyong Sun, Dartmouth (CA); Roberto E. Armenta, Darmouth (CA)

(73) Assignee: Mara Renewables Corporation, Dartmouth (CA)

(*) Notice: Subject to any disclaimer, the term of this patent is extended or adjusted under 35 U.S.C. 154(b) by 277 days.

(21) Appl. No.: 15/079,735

(22) Filed: Mar. 24, 2016

(65) Prior Publication Data

US 2016/0281054 A1 Sep. 29, 2016

Related U.S. Application Data

(60) Provisional application No. 62/138,631, filed on Mar. 26, 2015.

(51) Int. Cl.
C12N 1/32 (2006.01)
C12N 1/12 (2006.01)
C12P 7/6427 (2022.01)
C12P 7/6472 (2022.01)

(52) U.S. Cl.
CPC ............ *C12N 1/32* (2013.01); *C12N 1/12* (2013.01); *C12P 7/6427* (2013.01); *C12P 7/6472* (2013.01)

(58) Field of Classification Search
CPC ....................................................... C12N 1/32
See application file for complete search history.

(56) References Cited

U.S. PATENT DOCUMENTS

| | | |
|---|---|---|
| 4,341,038 A | 7/1982 | Bloch et al. |
| 4,680,314 A | 7/1987 | Nonomura |
| 4,952,511 A | 8/1990 | Radmer |
| 5,070,018 A | 12/1991 | Peters et al. |
| 5,104,803 A | 4/1992 | Delente |
| 5,130,242 A | 7/1992 | Barclay |
| 5,151,347 A | 9/1992 | Delente et al. |
| 5,162,051 A | 11/1992 | Hoeksema |
| 5,164,308 A | 11/1992 | Kyle |
| 5,168,056 A | 12/1992 | Frost |
| 5,171,680 A | 12/1992 | Mullenbach et al. |
| 5,244,921 A | 9/1993 | Kyle et al. |
| 5,272,073 A | 12/1993 | Frost et al. |
| 5,324,658 A | 6/1994 | Cox et al. |
| 5,340,594 A | 8/1994 | Barclay |
| 5,340,742 A | 8/1994 | Barclay |
| 5,374,657 A | 12/1994 | Kyle |
| 5,376,540 A | 12/1994 | Kyle |
| 5,397,591 A | 3/1995 | Kyle et al. |
| 5,407,957 A | 4/1995 | Kyle et al. |
| 5,466,434 A | 11/1995 | Kyle |
| 5,487,987 A | 1/1996 | Frost et al. |
| 5,492,938 A | 2/1996 | Kyle et al. |
| 5,518,918 A | 5/1996 | Barclay |
| 5,539,133 A | 7/1996 | Kohn et al. |
| 5,547,699 A | 8/1996 | Iizuka et al. |
| 5,550,156 A | 8/1996 | Kyle |
| 5,567,732 A | 10/1996 | Kyle et al. |
| 5,583,019 A | 12/1996 | Barclay |
| 5,616,496 A | 4/1997 | Frost et al. |
| 5,629,181 A | 5/1997 | Frost et al. |
| 5,656,319 A | 8/1997 | Barclay |
| 5,658,767 A | 8/1997 | Kyle |
| 5,688,500 A | 11/1997 | Barclay |
| 5,698,244 A | 12/1997 | Barclay |
| 5,711,983 A | 1/1998 | Kyle et al. |
| 5,882,703 A | 3/1999 | Barclay |
| 5,908,622 A | 6/1999 | Barclay |
| 5,985,348 A | 11/1999 | Barclay |
| 6,027,900 A | 2/2000 | Alinutt et al. |
| 6,054,147 A | 4/2000 | Barclay et al. |
| 6,103,225 A | 8/2000 | Barclay |

(Continued)

FOREIGN PATENT DOCUMENTS

| | | |
|---|---|---|
| CN | 101389749 | 3/2009 |
| CN | 102834523 | 12/2012 |

(Continued)

OTHER PUBLICATIONS

Thraustochytriaceae Family Data Sheet, 2007, 2 pages.
Omega-3 News, Ocean Nutrition Canada Ltd., 2011, 3 pages.
Breakthrough Process to Extract Oil from Algae, http://www.miningtopnews.com/originoil-announces-breakthrough-process-to-extract-oil-from-.htm., Apr. 20, 2009, 4 pages.
Oil from Algae, Oilgae Glossary, Available online at http://www.oilgae.com/algae/oil/extract/extract.html, Jun. 4, 2009, 8 pages.
Bajpai et al., Optimization of production of docosahexaenoic acid (DHA) by Thraustochytrium aureum ATCC 34304, Journal of the American Oil Chemists Society, vol. 68, Issue 7, Jul. 1991, pp. 509-514.

(Continued)

*Primary Examiner* — Vera Afremova
(74) *Attorney, Agent, or Firm* — Kilpatrick Townsend & Stockton LLP

(57) ABSTRACT

Provided is a method of culturing one or more microorganisms. The method includes culturing one or more microorganisms in a medium comprising crude glycerol at a first concentration level, feeding to the media an additional amount of crude glycerol, once the first concentration of glycerol is reduced to a first threshold level, at a concentration sufficient to achieve the first concentration level, monitoring the crude glycerol concentration until the first concentration level of the crude glycerol is reduced to the first threshold level. The steps may be repeated until a desired microorganism cell density is achieved.

28 Claims, 2 Drawing Sheets

Specification includes a Sequence Listing.

(56) References Cited

U.S. PATENT DOCUMENTS

| | | | |
|---|---|---|---|
| 6,140,365 | A | 10/2000 | Kiy et al. |
| 6,140,486 | A | 10/2000 | Facciotti et al. |
| 6,166,230 | A | 12/2000 | Bijl et al. |
| 6,166,231 | A | 12/2000 | Hoeksema |
| 6,177,108 | B1 | 1/2001 | Barclay |
| 6,180,376 | B1 | 1/2001 | Liddell |
| 6,255,505 | B1 | 7/2001 | Bijl et al. |
| 6,350,890 | B1 | 2/2002 | Kiy et al. |
| 6,372,460 | B1 | 4/2002 | Gladue et al. |
| 6,395,778 | B1 | 5/2002 | Luthria |
| 6,399,803 | B1 | 6/2002 | Corley et al. |
| 6,410,281 | B1 | 6/2002 | Barclay |
| 6,410,282 | B1 | 6/2002 | Kumar et al. |
| 6,441,208 | B2 | 8/2002 | Bijl et al. |
| 6,451,567 | B1 | 9/2002 | Barclay |
| 6,461,839 | B2 | 10/2002 | Yokochi et al. |
| 6,509,178 | B1 | 1/2003 | Tanaka et al. |
| 6,541,049 | B2 | 4/2003 | Barclay |
| 6,566,123 | B1 | 5/2003 | Barclay |
| 6,568,351 | B1 | 5/2003 | Barclay et al. |
| 6,582,941 | B1 | 6/2003 | Yokochi et al. |
| 6,596,766 | B1 | 6/2003 | Igarashi et al. |
| 6,607,900 | B2 | 8/2003 | Bailey et al. |
| 6,727,373 | B2 | 4/2004 | Bijl et al. |
| 6,749,849 | B2 | 6/2004 | Barclay |
| 6,750,048 | B2 | 6/2004 | Ruecker et al. |
| 6,783,951 | B2 | 8/2004 | Long, II |
| 6,812,009 | B2 | 11/2004 | Gladue et al. |
| 6,977,167 | B2 | 12/2005 | Barclay |
| 7,001,772 | B2 | 2/2006 | Roessler et al. |
| 7,005,280 | B2 | 2/2006 | Barclay |
| 7,011,962 | B2 | 3/2006 | Barclay |
| 7,022,512 | B2 | 4/2006 | Barclay |
| 7,033,584 | B2 | 4/2006 | Barclay |
| 7,063,855 | B2 | 6/2006 | Hjaltason et al. |
| 7,067,145 | B2 | 6/2006 | Place et al. |
| 7,247,461 | B2 | 7/2007 | Metz et al. |
| 7,259,006 | B2 | 8/2007 | Komazawa et al. |
| 7,351,558 | B2 | 4/2008 | Ruecker et al. |
| 7,374,908 | B2 | 5/2008 | Yamaoka |
| 7,381,558 | B2 | 6/2008 | Barclay |
| 7,419,596 | B2 | 9/2008 | Dueppen et al. |
| 7,514,244 | B2 | 4/2009 | Tanaka et al. |
| 7,923,226 | B2 | 4/2011 | Frost |
| 7,989,195 | B2 * | 8/2011 | Chi ............... C12P 7/6409 435/257.1 |
| 8,163,515 | B2 * | 4/2012 | Burja ............... A21D 8/04 435/41 |
| 8,168,225 | B2 | 5/2012 | Casaña Giner et al. |
| 8,202,713 | B2 | 6/2012 | Wen et al. |
| 8,541,210 | B2 | 9/2013 | Wen et al. |
| 2003/0060509 | A1 | 3/2003 | Elswyk |
| 2003/0143659 | A1 | 7/2003 | Bijl et al. |
| 2003/0180898 | A1 | 9/2003 | Bailey et al. |
| 2004/0067574 | A1 | 4/2004 | Bijl et al. |
| 2006/0094089 | A1 | 5/2006 | Barclay |
| 2008/0155888 | A1 | 7/2008 | Vick et al. |
| 2008/0220515 | A1 | 9/2008 | McCall |
| 2009/0029445 | A1 | 1/2009 | Eckleberry et al. |
| 2009/0077863 | A1 | 3/2009 | Oyler |
| 2009/0081748 | A1 | 3/2009 | Oyler |
| 2009/0117194 | A1 | 5/2009 | Burja et al. |
| 2010/0099901 | A1 | 4/2010 | Hayashi et al. |
| 2012/0244584 | A1 | 9/2012 | Zhang et al. |
| 2012/0317877 | A1 * | 12/2012 | Rangaswamy ......... C12P 7/649 44/385 |
| 2013/0089901 | A1 | 4/2013 | Seo et al. |
| 2013/0217084 | A1 | 8/2013 | Wen |
| 2014/0088317 | A1 | 3/2014 | Wen |

FOREIGN PATENT DOCUMENTS

| | | |
|---|---|---|
| CN | 103025862 | 4/2013 |
| WO | 1987003899 A1 | 7/1987 |
| WO | 1989000606 A1 | 1/1989 |
| WO | 1992013086 A1 | 8/1992 |
| WO | 1997037032 A2 | 10/1997 |
| WO | 2000005395 A1 | 2/2000 |
| WO | 2000054575 A2 | 9/2000 |
| WO | 2002010322 A1 | 2/2002 |
| WO | 2002092540 A1 | 11/2002 |
| WO | 2007068997 A2 | 6/2007 |
| WO | 2007069078 A2 | 6/2007 |
| WO | 2007074479 A1 | 7/2007 |
| WO | 2008090989 A1 | 7/2008 |
| WO | 2008129358 A2 | 10/2008 |
| WO | 2009034124 A1 | 3/2009 |
| WO | 2014137538 | 9/2014 |

OTHER PUBLICATIONS

Bajpai et al., Production of docosahexaenoic acid by Thraustochytrium aureum, Applied Microbiology and Biotechnology, vol. 35, Issue 6, Sep. 1991, pp. 706-710.

Baldwin, Application for the Approval of DHA-rich Oil, Omega Tech GmbH, Version No. Draft, 1997, 104 pages.

Barclay et al., Heterotrophic production of long chain omega-3 fatty acids utilizing algae and algae-like microorganisms, Journal of Applied Phycology, vol. 6, Issue 2, Apr. 1994, pp. 123-129.

Bateman et al., Method for Extraction and Separation by Solid Phase Extraction of Neutral Lipid, Free Fatty Acids, and Polar Lipid from Mixed Microbial Cultures, Journal of Agricultural and Food Chemistry, Jan. 20, 1997, pp. 132-134.

Bligh et al., A Rapid Method of Total Lipid Extraction and Purification, Canadian Journal of Biochemistry and Physiology, vol. 37, Issue 8, 1959, pp. 911-917.

Bowles et al., Long-chain n-3 polyunsaturated fatty acid production by members of the marine protistan group the thraustochytrids: screening of isolates and optimisation of docosahexaenoic acid production, Journal of Biotechnology, vol. 70, Issues 1-3, Apr. 1999, pp. 193-202.

Burja et al., Evaluation of fatty acid extraction methods for *Thraustochytrium* sp. ONC-T18, J. Agric. Food Chem., vol. 55, Issue 12, May 12, 2007, pp. 4795-4801.

Burja et al., Isolation and characterization of polyunsaturated fatty acid producing *thraustochytrium* species: screening of strains and optimization of omega-3 production, Applied Microbiology and Biotechnology, vol. 72, Issue 6, Oct. 2006, pp. 1161-1169.

Fu et al., Study on Production of EPA and DHA in Microbe Fermentation, Grain Processing, Issue 1, 2004, pp. 48-51.

Hauvermale et al., Fatty Acid Production in *Schizochytrium* sp.: Involvement of a Polyunsaturated Fatty Acid Synthase and a Type 1 Fatty Acid Synthase, Lipids, vol. 41, Issue 8, XP002581593, 2006, pp. 739-747.

Iida et al., Improvement of docosahexaenoic acid production in a culture of Thraustochytrium aureum by medium optimization, Journal of Fermentation and Bioengineering, vol. 81, Issue 1, 1996, pp. 76-78.

Kaulmann et al., Biosynthesis of Polyunsaturated Fatty Acids by Polyketide Synthases, Angewandte Chemie International Edition, vol. 41, Issue 11, Jun. 3, 2002, pp. 1866-1869.

Lewis et al., Evaluation of extraction methods for recovery of fatty acids from lipid-producing microheterotrophs, Journal of Microbiological Methods, vol. 43, Issue 2, Dec. 15, 2000, pp. 107-116.

Li et al., Production of docosahexaenoic acid by Thraustochytrium roseum, Journal of Industrial Microbiology, vol. 13, Issue 4, Aug. 1994, pp. 238-241.

Liu, Study on Production of EPA and DHA in Microbe Fermentation, Food Science and Technology, No. 6, 2004, pp. 13-16.

Marine Biopharmacy, Marine Biopharmacy fermentation engineering, Beijing Chemical Industry Press, 2002, pp. 96-101.

Metz et al., Production of polyunsaturated fatty acids by polyketide synthases in both prokaryotes and eukaryotes, Science, vol. 293, Issue 5528, Jul. 2001, pp. 290-293.

Molina Grima et al., Recovery of microalgal biomass and metabolites: process options and economics, Biotechnology Advances, vol. 20, Issues 7-8, Jan. 2003, pp. 491-515.

(56) References Cited

OTHER PUBLICATIONS

Nakahara et al., Production of docosahexaenoic and docosapentaenoic acids by*Schizochytrium* sp. isolated from Yap Islands, Journal of the American Oil Chemists' Society, vol. 73, Issue 11, Nov. 1996, pp. 1421-1426.
Pinkart et al., Rapid separation of microbial lipids using solid phase extraction columns, Journal of Microbiological Methods, vol. 34, Issue 1, Sep. 1, 1998, pp. 9-15.
Ratledge et al., Single cell oils—A coming of age, Lipid Technology, vol. 16, Feb. 2004, pp. 34-39.
Sijtsma et al., Recent advances in fatty acid synthesis in oleaginous yeasts and microalgae, Recent Research Developments in Microbiology, vol. 2, Jan. 1998, pp. 219-232.
Singh et al., Docosahexaenoic acid (DHA) production by *Thraustochytrium* sp. ATCC 20892, World Journal of Microbiology and Biotechnology, vol. 12, Issue 1, Jan. 1996, pp. 76-81.
Song et al., Effective Phase Separation of Biomass Pyrolysis Oils by Adding Aqueous Salt Solutions, Energy and Fuels, vol. 23, 2009, pp. 3307-3312.
Wardencki et al., Trends in solventless sample preparation techniques for environmental analysis, Journal of Biochemical and Biophysical Methods, vol. 70, Issue 2, 2007, pp. 275-288.
Yamaoka et al., Growth Characterization and Resources of Thraustochytrium CHN-1 Isolated from the Seto Inland Sea, Bulletin of the Society of Sea Water Science, Japan, vol. 59, No. 1, 2005, pp. 23-31.
Yokochi et al., Optimization of docosahexaenoic acid productions by Schizochytrium limacinum SR21, Applied Microbiology and Biotechnology, vol. 49, Issue 1, Jan. 1998, pp. 72-76.
Thompson, et al., "Characterization of Crude Glycerol from Biodiesel Production from Multiple Feedstocks," Applied Engineering in Agriculture, vol. 22(2) pp. 261-265, 2006.
Hu, et al., "Characterization of Crude Glycerol from Biodiesel Plants," J. Agric. Food Chem., 2012, 60(23): 5915-5921 (2012).
Pyle et al., "Producing Docosahexaenoic Acid (DHA)-rich Algae from Biodiesel-Derived Crude Glycerol: Effects of Impurities on DHA Production and Algal Biomass Composition," Journal of Agricultural and Food Chemistry, 2008, 56, pp. 3933-3939.
Liang, et a., "Batch Stage Study of Lipid Production from Crude Glycerol Derived from Yellow Grease or Animal Fats Through Microalgal Fermentation," Bioresource Technology 101 (2010) pp. 6745-6750.
Cheirsilp, et al., "Co-Culture of an Oleaginous Yeast Rhodotorula Glutinis and a Microalga Chlorella Vulgaris for Biomass and Lipid Production Using Pure and Crude Glycerol as a Sole Carbon Sournce," Ann. Microbio., vol. 62, pp. 987-993, 2012.
Ethier, et al., "Continuous Culture of the Microalgae Schizochytrium Limaacinum on Biodiesel-Derived Crude Glycerol for producing Docosahexaenoic Acid," Bioresourc. Technol., vol. 102, pp. 88-93, 2011.
Kong, et al., "Effect of Glycerol and Glucose on the Enhancement of Biomass, Lipid and Solumble Carbohydrate Production by Cholrella Vulgaris in Mixotrophic Culture," Food. Technol. Biotechnol., vol. 51, No. 1, pp. 62-69, 2013.
Chang, et al., "Improvement of Docosahexaenoic Acid Production on Glycerol by *Schizochytrium* sp. S31 with Constantly High Oxygen Transfer Coefficient," Bioresource Technology 142 (2013) pp. 400-406.
Chi et al., Process Biochemistry 42:1537-1545 (2007).
CL201702380 , "Office Action", dated Feb. 26, 2019, 23 pages.
CL2017-2380 , "Office Action", dated Oct. 12, 2018, 24 pages.
EP16767853.1 , "Extended European Search Report", dated Sep. 21, 2018, 6 pages.
SG11201707234S , "Written Opinion", dated Jul. 2, 2018, 8 pages.
JP2017-550112 , "Office Action", dated Jul. 30, 2019, 10 pages.
SG11201707234S , "Notice of Decision to Grant", dated Jul. 17, 2019, 6 pages.
Application No. ARP160100766, Office Action, dated Jun. 10, 2020, 4 pages.
AU2016238396, "First Examination Report", dated Aug. 18, 2020, 4 pages.
AU2016238396, "Second Examination Report", dated Dec. 16, 2020, 5 pages.
Application No. CA2,980,679, Office Action, dated Jan. 29, 2020, 6 pages.
Application No. CA2,980,679, Office Action, dated Mar. 9, 2021, 8 pages.
Chi et al., "Study of a Two-Stage Growth of Dha-Producing Marine Algae Schizochytrium Limacinum Sr21 with Shifting Dissolved Oxygen Level", Applied Microbial and Cell Physiology, vol. 81, No. 6, Jan. 1, 2009, pp. 1141-1148.
Application No. CN201680017603.X, Office Action, dated Feb. 23, 2021, 10 pages.
Application No. CN201680017603.X, Office Action, dated Apr. 13, 2020, 11 pages.
Application No. CN201680017603.X, Office Action, dated Jun. 30, 2021, 16 pages.
Application No. JP2017-550112, Office Action, dated Mar. 10, 2020, 12 pages.
Application No. JP2017-550112, Office Action, dated Jun. 15, 2021, 5 pages.
Application No. KR10-2017-7030585, Office Action, dated Feb. 20, 2021, 4 pages.
Application No. KR2017-7030585, Office Action, dated Jun. 30, 2020, 6 pages.
Application No. MX/a/2017/011516, Office Action, dated Feb. 17, 2022, 4 pages.
Application No. MX/A/2017/011516, Office Action, dated Apr. 4, 2022, 4 pages.

* cited by examiner

HIGH DENSITY PRODUCTION OF BIOMASS AND OIL USING CRUDE GLYCEROL

CROSS REFERENCE TO RELATED APPLICATIONS

This application claims priority to U.S. Provisional Application No. 62/138,631, filed Mar. 26, 2015, which is incorporated by reference herein in its entirety.

BACKGROUND

Heterotrophic fermentations of microorganisms are efficient way of generating high value oil and biomass products. Under certain cultivation conditions, microorganisms synthesize intracellular oil, which can be extracted and used to produce biofuel (e.g., biodiesel, bio-jetfuel, and the like) and nutritional lipids (e.g., polyunsaturated fatty acids such as DHA, EPA, and DPA). The biomass of some microorganisms is also of great nutritional value due to high polyunsaturated fatty acid (PUFA) and protein content, and can be used as a nutritional supplement for animal feed. However, heterotrophic fermentation is an intensive process of high cost, and high energy and feedstock consumption. Carbon feedstock cost is typically a very significant portion of the total cost for producing microorganism biomass and oil. Existing microorganism fermentations use mainly expensive carbohydrates, such as glucose, as the carbon source. Cheaper carbon alternatives are being investigated in order to make the production process economically favorable. Besides glucose, several other forms of carbon, such as fructose and glycerol, are natural carbon substrates for microorganisms. However, highly purified glycerol costs more than glucose.

BRIEF SUMMARY

Provided is a method of culturing one or more microorganisms. The method includes culturing one or more microorganisms in a medium comprising crude glycerol at a first concentration level, feeding to the media an additional amount of crude glycerol, once the first concentration of glycerol is reduced to a first threshold level, at a concentration sufficient to achieve the first concentration level, monitoring the crude glycerol concentration until the first concentration level of the crude glycerol is reduced to the first threshold level. The steps may be repeated until a desired microorganism cell density is achieved.

Also provided is a method for producing one or more fatty acids. The methods include providing a microorganism capable of producing fatty acids, providing a media comprising crude glycerol, and culturing the microorganism in the media under sufficient conditions to produce the one or more fatty acids to provide a final concentration of the one or more unsaturated fatty acids that is at least 50% by weight of the microorganisms.

DETAILED DESCRIPTION

Figure 1:
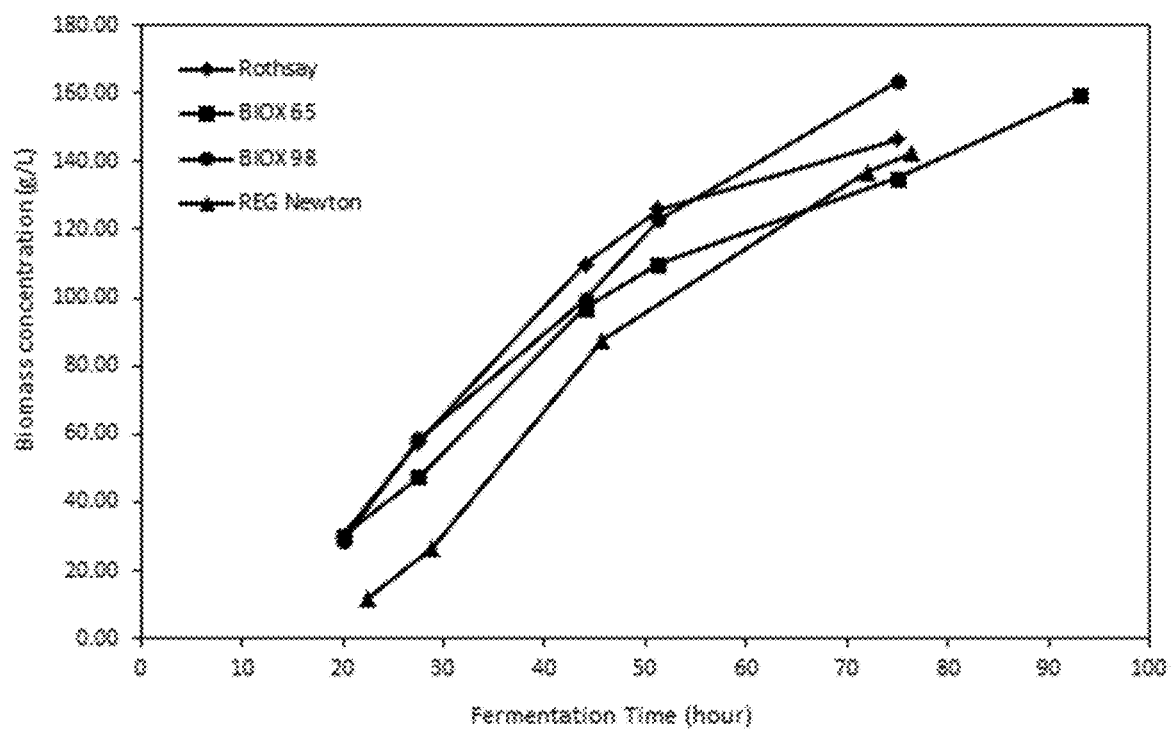
FIG. 1 is a graph showing the biomass concentration (g/L) over time profile during fermentations using various crude glycerol feedstocks from different biodiesel producers as the only carbon source.

The increased worldwide demand and production capacity for biofuel has resulted in a huge surplus of crude glycerol as a by-product. Refining crude glycerol requires too great an investment, while unrefined crude glycerol has very little economic value. Consequently, many manufacturers of biofuel consider crude glycerol to be a type of industrial wastewater. Therefore, an efficient process to convert such crude glycerol into higher-valued products would be of great interest. Although biodiesel by-product glycerol (a type of crude glycerol) has been used as a carbon source, high density biomass and oil has not been achieved due to the toxicity caused by crude glycerol impurities and the lack of proper fermentation carbon supply strategy for avoiding such toxicity. In contrast, provided herein are methods of culturing microorganisms and producing oil using crude glycerol. The provided methods resulted in high biomass and oil production achieving 172 g/L dry cell weight containing 68% oil during fermentation. Such productivities are comparable to what can be achieved by glucose-based fed-batch fermentations.

Thus, the provided methods enable growing microorganisms to a high cell density (>100 g/L) and high oil content (>50%) using the industrial by-product, glycerol (crude), as a partial or sole carbon substrate combined with other nutrient ingredients. The crude glycerol from industrial sources requires little to no pretreatment. Crude glycerol substrate is fed into the fermentor by a defined and controlled manner such that any biological inhibitory effect can be kept at minimum while very high biomass and oil yield can be achieved. It is also demonstrated herein that, the typical sterilization procedure required for aseptic fermentation processes can be removed. Also pretreatment of the crude glycerol can be reduced or eliminated and the glycerol can be fed to the microorganism culture as it is when received from the manufacturer. This saves significant energy cost when such a process is carried out at a commercial scale. As used herein, the term "pretreatment" refers to the removal of non-glycerol impurities that could physically or biologically impact the culture growth. Examples of pretreatment include chemical treatment to precipitate and remove impurities, pH adjustment to match the pH of the culture environment, filtration or centrifugation to remove suspended solid.

Provided herein is a method of culturing one or more microorganisms. The methods include culturing one or more microorganisms in a medium comprising crude glycerol at a first concentration level, feeding to the media an additional amount of crude glycerol, once the first concentration of glycerol is reduced to a first threshold level, at a concentration sufficient to achieve the first concentration level, monitoring the crude glycerol concentration until the first concentration level of the crude glycerol is reduced to the first threshold level. Optionally, the first concentration level is between 1 and 60 g/L, or any level between 1 and 60 g/L, inclusive. Optionally, the first concentration level is between 5 and 60 g/L, between 15 and 60 g/L, between 5 and 20 g/L, or between 15 and 20 g/L. Optionally, the first threshold level is between 0 and 5 g/L or any level between 0 and 5 g/L, inclusive. Thus, the first threshold level can be, for example, 0, 1, 2, 3, 4, or 5 g/L. Optionally, the steps are repeated until desired microorganism cell density is achieved. Optionally, the desired microorganism cell density is greater than 100 g/L. Optionally, the desired cell density is from 50 to 200 g/L, 50 to 150 g/L, 50 to 100 g/L, 100 to 250 g/L, 100 to 150 g/L, or 80 to 100 g/L. Optionally, the cell density is any density between 50 to 250 g/L, inclusive. Optionally, the cell density is from 80 to 100 g/L. Optionally, the cell density is from 120 to 230 g/L. Optionally, the microorganism cell density contains 50% to 80% by weight of total fatty acids. Optionally, the total fatty acids comprise 10 to 45% DHA. Optionally, the microorganism cell density contains 5 to 36% DHA by total cell weight.

The microorganisms are capable of producing one or more fatty acids. Thus, provided are methods for producing one or more fatty acids. The methods include providing a microorganism capable of producing fatty acids, providing a media comprising crude glycerol, and culturing the microorganism in the media under sufficient conditions to produce the one or more fatty acids to provide a final concentration of the one or more unsaturated fatty acids that is at least 50% by weight of the microorganisms. Optionally, the fatty acids are polyunsaturated fatty acids. The polyunsaturated fatty acids can be, for example, alpha linolenic acid, arachidonic acid, docosahexanenoic acid, docosapentaenoic acid, eicosapentaenoic acid, gamma-linolenic acid, linoleic acid, linolenic acid, and combinations thereof.

In the provided methods, monitoring the crude glycerol concentration can be carried out using a variety of methods known to those of skill in the art. Optionally, the monitoring comprises measuring dissolved oxygen levels. Optionally, the monitoring comprises obtaining a sample of the media and determining the glycerol concentration in the sample. Optionally, the monitoring comprises analyzing the sample using calorimetric assay, chemical reaction based calorimetric assay, fluorescence assay, HPLC assay, enzymatic assay, or combinations thereof.

There are a variety of microorganisms suitable for use in the provided methods. The microorganisms described herein can be algae (e.g., microalgae), fungi (including yeast), bacteria, or protists. Optionally, the microorganism includes Thraustochytrids of the order *Thraustochytriales*, and, more specifically, *Thraustochytriales* of the genus *Thraustochytrium*. Optionally, the population of microorganisms includes *Thraustochytriales* as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18) as described in U.S. Pat. No. 8,163,515, which is incorporated by reference herein in its entirety. Thus, the microorganism can have an 18s rRNA sequence that is at least 95%, 96%, 97%, 98%, 99%, 99.1%, 99.2%, 99.3%, 99.4%, 99.5%, 99.6%, 99.7%, 99.8%, 99.9% or more (e.g., including 100%) identical to SEQ ID NO:1.

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyls (e.g., oxycarotenoids), hydrocarbons, and other lipids known to one of ordinary skill in the art. Optionally, the lipid compounds include unsaturated lipids. The unsaturated lipids can include polyunsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, polyunsaturated and highly unsaturated compounds. being inoculated with a 10% seed volume this long lag phase is dramatically shortened.

The provided methods include or can be used in conjunction with additional steps for culturing microorganisms according to methods known in the art. For example, a Thraustochytrid, e.g., a *Thraustochytrium* sp., can be cultivated according to methods described in U.S. Patent Publications 2009/0117194 or 2012/0244584, which are herein incorporated by reference in their entireties for each step of the methods or composition used therein.

Microorganisms are grown in a growth medium (also known as "culture medium"). Any of a variety of medium can be suitable for use in culturing the microorganisms described herein. Optionally, the medium supplies various nutritional components, including a carbon source and a nitrogen source, for the microorganism. Medium for Thraustochytrid culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine.

Figure 4:
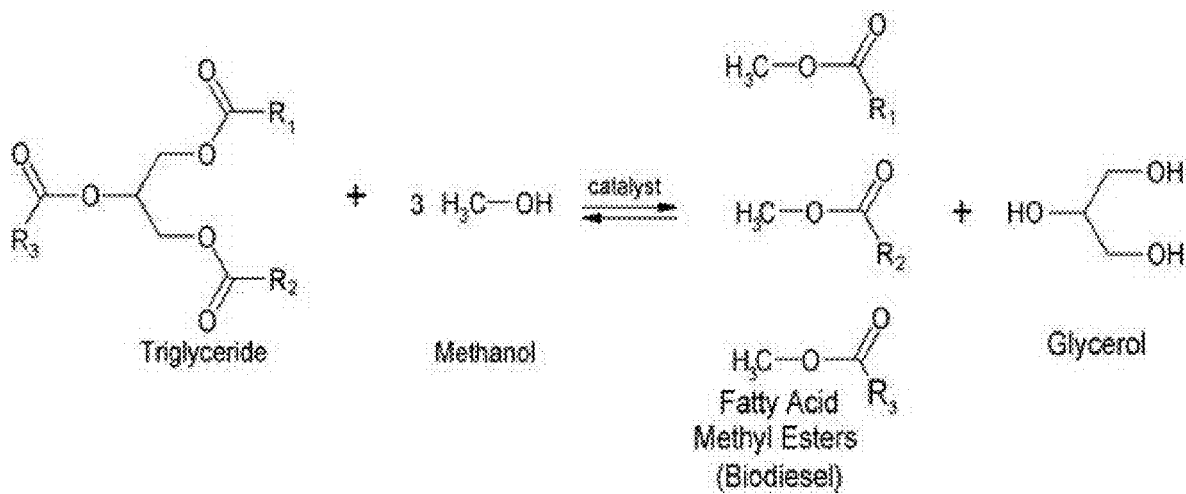
FIG. 4 is a schematic of a methanol-based biodiesel transesterification reaction.

The medium or media used in the provided methods comprises crude glycerol. As used herein, the term "crude glycerol" refers to a byproduct of a manufacturing process, e.g., biodiesel production. The term "crude glycerol" is distinguished from the terms "glycerol" or "glycerin" since these products comprise solely or essentially "glycerol" or "glycerin" in pure form. The terms "glycerol" and "glycerin" are used herein interchangeably throughout. Thus, crude glycerol contains additional agents and/or ingredients from pure glycerol or glycerin. Optionally, the crude glycerol is a byproduct of biodiesel production. Crude glycerol is the major byproduct of biodiesel production via triglycerides transesterification, or the byproduct of soap production via hydrolysis (saponification) of triglycerides. For example, a typical biodiesel process is the reaction of fat or oil (triglycerides) with an alcohol such as methanol to form esters of fatty acids (biodiesel) and glycerol. A methanol-based reaction example is shown in FIG. 4. Due to the impurities in the fat/oil, as well as the reaction itself, which are often aided by chemical catalysts such as sodium methylate, the final glycerol fraction contains relatively high content of impurities. A typical crude glycerol's composition and physical properties are shown in Table 1 (Reference: REG Ralston crude glycerol certificate of analysis). The ash composition of the same crude glycerol is shown in Table 2.

More examples of crude glycerol characterizations can be found in reference by Thompson and He, Applied Engineering in Agriculture, Vol. 22(2): 261-265 (2006), and by Hu et al., J. Agric. Food Chem., 2012, 60(23):5915-5921 (2012), which are incorporated by reference herein in their entireties.

TABLE 1

REG Ralston crude glycerol byproduct.

| Components | Value | Units | Test Method |
| --- | --- | --- | --- |
| Glycerin content | 80.5 | % mass | AOCS Ca 14-56/USP |
| Methanol content | 0.01 | % mass | AOCS Ba 13-87 modified |
| Water content | 12.8 | % mass | AOCS Ca 2e-84 |
| Ash | 6.6 | % mass | AOCS Ca 11-55 |
| Total fatty acid content | 0.08 | % mass | AOCS Ca 5b-71 |
| MONG (Matter Organic Not Glycerin) | 0.1 | % mass | Calculated value, by subtracting glycerin, water, and ash from 100% |
| pH | 4.3 | n/a | pH meter |
| Gardner color | 5 | n/a | ASTM D1544 |

TABLE 2

Ash composition of REG's Ralston crude glycerol byproduct.

| Analytes | Unit | Value |
| --- | --- | --- |
| Calcium | mg/kg | 10 |
| Iron | mg/kg | 2 |
| Magnesium | mg/kg | 2 |
| Potassium | mg/kg | 14 |
| Sodium | mg/kg | 25100 |
| Zinc | mg/kg | 0.5 |

Optionally, the crude glycerol is the only carbon source in the medium or media. Optionally, the medium comprises one or more additional carbon sources. Optionally, the crude glycerol is not sterilized or pretreated. Optionally, the crude glycerol comprises methanol, water, ash, non-glycerin organic matter, sodium sulphate, methyl tallowate, or a combination thereof. Optionally, the ash comprises calcium, iron, magnesium, potassium, sodium, zinc or a combination thereof.

Optionally, the microorganisms provided herein are cultivated under conditions that increase biomass and/or production of a compound of interest (e.g., oil or total fatty acid (TFA) content). Thraustochytrids, for example, are typically cultured in saline medium. Optionally, Thraustochytrids can be cultured in medium having a salt concentration from about 0.5 g/L to about 50.0 g/L. Optionally, Thraustochytrids are cultured in medium having a salt concentration from about 0.5 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 0.5 g/L to about 20 g/L (e.g., from about 0.5 g/L to about 15 g/L). The culture medium optionally includes NaCl. Optionally, the medium includes natural or artificial sea salt and/or artificial seawater.

The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is supplied by sodium chloride.

Optionally, the culture medium has chloride concentrations of less than about 3 g/L, 500 mg/L, 250 mg/L, or 120 mg/L. For example, culture medium for use in the provided methods can have chloride concentrations of between and including about 60 mg/L and 120 mg/L.

Medium for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Optionally, the resulting biomass is pasteurized to inactivate undesirable substances present in the biomass. For example, the biomass can be pasteurized to inactivate compound degrading substances. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 95° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means, such as, for example, by direct steam injection.

Optionally, no pasteurization step is performed. Stated differently, the method taught herein optionally lacks a pasteurization step.

Optionally, the biomass can be harvested according to a variety of methods, including those currently known to one skilled in the art. For example, the biomass can be collected from the fermentation medium using, for example, centrifugation (e.g., with a solid-ejecting centrifuge) or filtration (e.g., cross-flow filtration). Optionally, the harvesting step includes use of a precipitation agent for the accelerated collection of cellular biomass (e.g., sodium phosphate or calcium chloride).

Optionally, the biomass is washed with water. Optionally, the biomass can be concentrated up to about 20% solids. For example, the biomass can be concentrated to about 5% to about 20% solids, from about 7.5% to about 15% solids, or from about solids to about 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

The provided methods, optionally, include isolating the polyunsaturated fatty acids from the biomass or microorganisms. Isolation of the polyunsaturated fatty acids can be performed using one or more of a variety of methods, including those currently known to one of skill in the art. For example, methods of isolating polyunsaturated fatty acids are described in U.S. Pat. No. 8,163,515, which is incorporated by reference herein in its entirety. Optionally, the medium is not sterilized prior to isolation of the polyunsaturated fatty acids. Optionally, sterilization comprises an increase in temperature. Optionally, the polyunsaturated fatty acids produced by the microorganisms and isolated from the provided methods are medium chain fatty acids. Optionally, the one or more polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

Oil including polyunsaturated fatty acids (PUFAs) and other lipids produced according to the method described herein can be utilized in any of a variety of applications exploiting their biological, nutritional, or chemical properties. Thus, the provided methods optionally include isolating oil from the harvested portion of the threshold volume. Optionally, the oil is used to produce fuel, e.g., biofuel. Optionally, the oil can be used in pharmaceuticals, food supplements, animal feed additives, cosmetics, and the like. Lipids produced according to the methods described herein can also be used as intermediates in the production of other compounds.

By way of example, the oil produced by the microorganisms cultured using the provided methods can comprise fatty acids. Optionally, the fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof. Optionally, the oil comprises triglycerides. Optionally, the oil comprises fatty acids selected from the group consisting of palmitic acid (C16:0), myristic acid (C14:0), palmitoleic acid (C16:1(n-7)), cis-vaccenic acid (C18:1(n-7)), docosapentaenoic acid (C22:5(n-6)), docosahexaenoic acid (C22:6(n-3)), and combinations thereof.

Optionally, the lipids produced according to the methods described herein can be incorporated into a final product (e.g., a food or feed supplement, an infant formula, a pharmaceutical, a fuel, etc.) Suitable food or feed supplements into which the lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods and the like; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFAs) can be incorporated into a nutraceutical or pharmaceutical. Examples of such a nutraceuticals or pharmaceuticals include various types of tablets, capsules, drinkable agents, etc. Optionally, the nutraceutical or pharmaceutical is suitable for topical application. Dosage forms can include, for example, capsules, oils, granula, granula subtilae, pulveres, tabellae, pilulae, trochisci, or the like.

The oil or lipids produced according to the methods described herein can be incorporated into products as described herein in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

As used throughout, ranges (e.g., 1-10) and references to about a given value (e.g., about 1 or about 10) includes the recited value or values (e.g., 1 and/or 10)

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1

Crude Glycerol Fermentation

Four streams of crude glycerol were obtained from three different biodiesel producers (Rothsay (Winnipeg, Canada), BIOX (Hamilton, Canada), and REG Newton LLC (Newton, Iowa)). Their compositions are listed in Table 3, based on information provided by the corresponding producers. It was clear that great variability exhibited among the different crude glycerol.

TABLE 3

Crude Glycerol Components of Crude Glycerol Byproduct from Biodiesel.

| | | Value | | | |
|---|---|---|---|---|---|
| Components | Units | Rothsay | BIOX 65 | BIOX 98 | REG Newton |
| Glycerin | % mass | 80 | 60~70 | >98 | 79.2 |
| Ash | % mass | 2.6 | n/a | n/a | 6.3 |
| Methanol | % mass | n/a | n/a | n/a | 0.1 |
| Moisture | % mass | 12.3 | trace | <2 | 12.4 |
| Free fatty acids | % mass | 1.7 | n/a | n/a | 0.04 |
| MONG | % mass | 3.4 | n/a | n/a | 1.96 |
| Sodium Sulphate | % mass | n/a | 16~20 | n/a | n/a |
| Methyl Tallowate | % mass | n/a | 2~10 | n/a | n/a |
| pH | n/a | 2.2 | 2.5 | 3.7 | 5.2 |

*MONG: matter-organic non-glycerin

To conduct lab scale fermentation experiment, the pH of Rothsay and BIOX 65 crude glycerol was adjusted to 5.5 using a sodium hydroxide solution. BIOX 98 and REG Newton crude glycerol was not pH adjusted. All crude glycerol streams were then autoclaved and used as the sole source of feeding carbon to carry out separate crude glycerol-based fed-batch fermentations of *Thraustochytrium* ONC-T18 in 2 L fermentors. All initial fermentation medium contained (per liter): glycerol 60 g, soy peptone 2 g; sodium chloride 1.65 g; magnesium sulfate heptahydrate 4 g; potassium phosphate monobasic 2.2 g; potassium phosphate dibasic 2.4 g; ammonium sulfate 20 g; calcium chloride dihydrate 0.1 g; iron chloride 0.003 g; copper sulfate pentahydrate 0.003 g; sodium molybdate dehydrate 0.0015 g; zinc sulfate heptahydrate 0.003 g; cobalt chloride hexahydrate 0.0015 g; manganese chloride tetrahydrate 0.0015 g; nickel sulfate hexahydrate 0.0015 g; vitamin B12 0.00003 g; biotin 0.00003 g; thiamin hydrochloride 0.006 g. The 2 L fermentors were used for the Rothsay, BIOX 65 and BIOX 98 fermentations, while a 5 L fermentor was used for the REG Newton fermentation. The pH of all fermentations were controlled at 4.5±0.2 by sodium hydroxide and phosphoric acid solutions. The temperature of all fermentations were controlled at 28° C. All fermentations were operated in fed-batch mode, using the corresponding crude glycerol as the only carbon feedstock. At the appropriate time, a dose of crude glycerol was automatically pumped into the fermentor to bring the in-medium glycerol concentration up to 60 g/L (for 2 L runs), or 20 g/L (for 5 L run).

Such carbon feeding was carried throughout the entire fermentation, until a certain biomass concentration and intracellular oil content have been reached. Final biomass concentrations ranging from 140 g/L to 165 g/L were attained (FIG. 1), containing intracellular lipids ranging from 65% to 78% (Table 4). Considering the quality variations among the tested crude glycerol feedstocks, and the minimum pre-treatment applied to them, these results were good demonstrations of the robustness of the developed high cell/lipid density fed-batch fermentation process for carrying out commercially viable biomass and lipid production using crude glycerol byproducts.

TABLE 4

Summary of Fermentation Results Using Various Crude Glycerol Feedstocks as the only Carbon Source.

| | | Value | | | |
|---|---|---|---|---|---|
| Metrics | Units | Rothsay | BIOX 65 | BIOX 98 | REG Newton |
| Fermentation time | hour | 75 | 93 | 75 | 76.4 |
| Final dry biomass | g/L | 146.63 | 159.29 | 163.43 | 142.49 |
| Final lipid content | % | 70.02 | 67.88 | 77.56 | 65.56 |
| Final lipid | g/L | 102.67 | 108.13 | 126.76 | 93.42 |
| Biomass productivity | g/L-d | 46.92 | 41.11 | 52.30 | 44.76 |
| Lipid productivity | g/L-d | 32.85 | 27.90 | 40.56 | 29.35 |

Example 2

Mixed Carbon Source Fermentation

Figure 2:
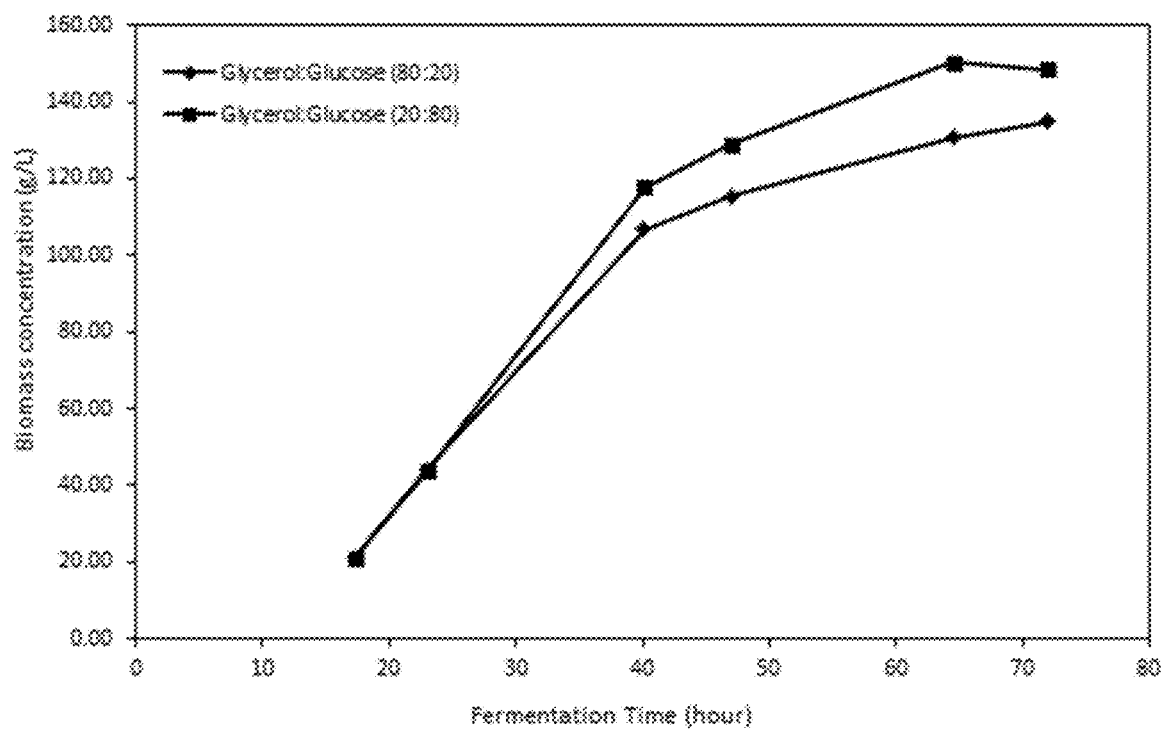
FIG. 2 is a graph showing the biomass concentration (g/L) over time profile during fermentations using a mixture of crude glycerol and glucose at different volume ratios. Glycerol means crude glycerol from Rothsay; glucose means 750 g/L glucose solution. The ratio was volume ratio of the two solutions.

Sufficient and uninterrupted quantity of carbon feedstock supply is of key importance for the operation of a fermentation-based production plant. Under circumstances when the main carbon feedstock is in short supply, being able to utilize supplement carbon feedstocks can be important to the sustained operation of the plant. Therefore, fermentations of *Thraustochytrium* ONC-T18 using a mixture of glucose and crude glycerol were conducted. Although glucose is a well-known carbon source for high density fermentation of Thraustochytrids for lipid production, it was not clear whether carbon catabolite repression would occur if glucose was used with a second carbon source in the same fermentation. Two 2 L fermentors were prepared using the initial medium formulation same as shown in Example 1. Crude glycerol from Rothway was obtained, with the specifications shown in Example 1; and a 750 g/L glucose solution was also prepared. Crude glycerol and the glucose solution were then physically mixed at 80:20 volume ratio as the carbon feed for the first fermentor, and mixed at 20:80 volume ratio as the feed for the second fermentor. The fermentations were conducted by the same carbon feeding strategy described in Example 1. As demonstrated by the data shown in FIG. 2 and Table 5, using crude glycerol and glucose as mixed carbon feed produced biomass and lipid results that were comparable to those when crude glycerol was used as the only carbon feed. Carbon catabolite repression, which is the phenomenon that the presence of a preferred carbon source inhibits the metabolization of a second carbon source when both carbons are present in the growth medium, was not found to be the case in this example. During the fermentations, both glycerol and glucose were consumed simultaneously throughout the cultivation process. This example demonstrates that during a commercial cultivation of Thraustochytrid, crude glycerol may be used as the major carbon source, or the minor carbon source, and a secondary carbon feedstock may be used in the same fermentation. Such flexibility in carbon usage ensures the stability of large scale fermentation process operation.

TABLE 5

Summary of Fermentation Results Using a Mixture of Crude Glycerol and Glucose at Different Volume Ratios.

| | | Value | |
|---|---|---|---|
| Metrics | Units | Crude glycerol:glucose (80:20) | Crude glycerol:glucose (20:80) |
| Fermentation time | hour | 72 | 72 |
| Final dry biomass | g/L | 134.84 | 148.59 |
| Final lipid content | % | 68.97 | 69.41 |
| Final lipid | g/L | 93.00 | 103.14 |
| Biomass productivity | g/L-d | 44.95 | 49.53 |
| Lipid productivity | g/L-d | 31.00 | 34.38 |

Example 3

Mixed Crude Glycerol Fermentation

Similar to Example 2, for sustained large scale plant operation, it would also be advantageous to be able to use mixtures of crude glycerol from different biodiesel manufacturing processes. To this end, four streams of crude glycerol were mixed at equal volume ratio to form a crude glycerol mixture. The specifications of each stream are listed in Table 6. After being mixed, the crude glycerol mixture was used as carbon feed without any further treatment (e.g. pH adjustment, filtration) or sterilization. A 30 L fermentor was prepared for this experiment, with the initial culture medium having a formulation the same as that shown in Example 1, except that no glycerol was batched in the initial medium before the sterilization procedure. Immediately following inoculation, the crude glycerol mixture was fed according to the feeding strategy described in Example 1, with each dosing bringing the in-medium glycerol concentration up to 20 g/L. By 70 hours, biomass reached 171.54 g/L, with 68.00% lipids. Despite being used without sterilization, the fermentation was free of contamination.

TABLE 6

Compositions of Crude Glycerol Byproduct from Different Biodiesel Manufacturing Processes to make a Crude Glycerol Mixture.

| | | Value | | | |
|---|---|---|---|---|---|
| Components | Units | Rothsay | BIOX 65 | REG Ralston | REG Newton |
| Glycerin | % mass | 80 | 60~70 | 80.5 | 79.2 |
| Ash | % mass | 2.6 | n/a | 6.6 | 6.3 |

TABLE 6-continued

Compositions of Crude Glycerol Byproduct from Different Biodiesel Manufacturing Processes to make a Crude Glycerol Mixture.

| | | Value | | | |
|---|---|---|---|---|---|
| Components | Units | Rothsay | BIOX 65 | REG Ralston | REG Newton |
| Methanol | % mass | n/a | n/a | 0.01 | 0.1 |
| Moisture | % mass | 12.3 | trace | 12.8 | 12.4 |
| Free fatty acids | % mass | 1.7 | n/a | 0.08 | 0.04 |
| MONG* | % mass | 3.4 | n/a | 0.1 | 1.96 |
| Sodium Sulphate | % mass | n/a | 16~20 | n/a | n/a |
| Methyl Tallowate | % mass | n/a | 2~10 | n/a | n/a |
| pH | n/a | 2.2 | 2.5 | 4.3 | 5.2 |

*MONG: matter-organic non-glycerin

Example 4

Crude Glycerol for Commercial Biomass and Lipid Production

Figure 3:
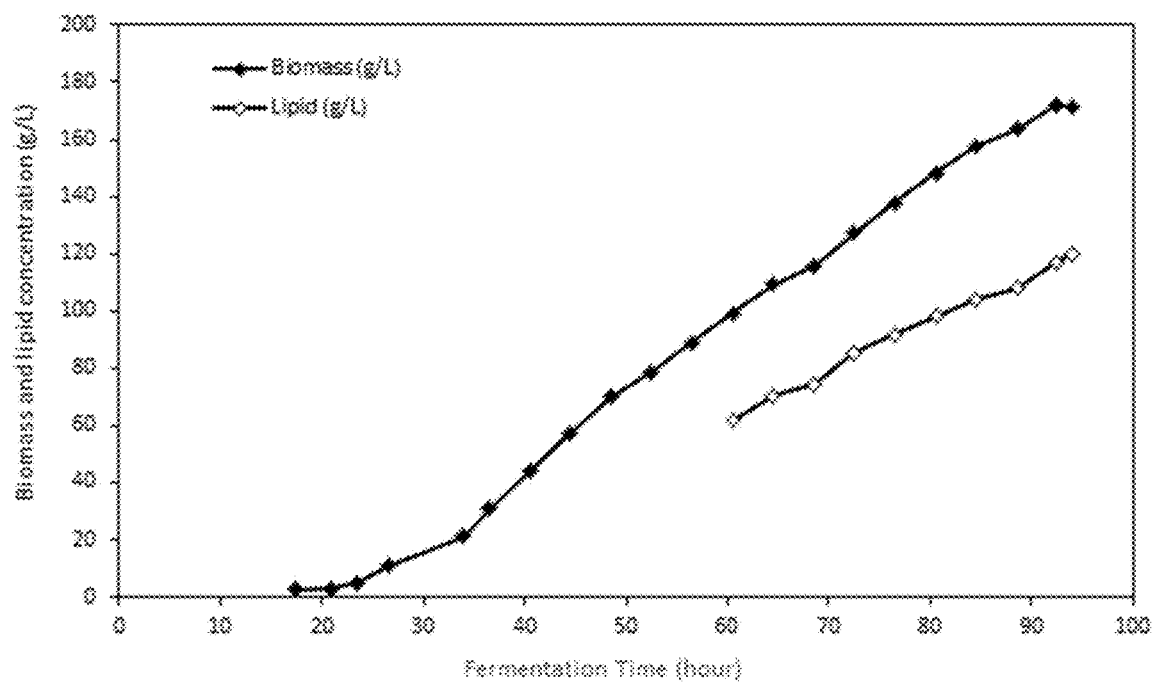
FIG. 3 is a graph showing the biomass and lipid concentration over time profile during a large-scale (200,000 L) fermentation of *Thraustochytrium* ONC-T18 using crude glycerol as the only feeding carbon source.

To prove the feasibility of the developed crude glycerol based fermentation process for commercial biomass and lipid production, two large scale (200,000 L) fermentations were conducted. REG Ralston crude glycerol was used as the only feeding carbon source, without any pretreatment or sterilization. The medium formulation was the same as described in Example 1, except that only 30 g/L glucose was batched into the initial medium, 1 g/L soy peptone was used in the first batch and 1 g/L corn steep solid (instead of soy peptone) was used in the second batch. The fermentation was conducted at pH 4.5±0.3, with temperature controlled at 29±1° C. Biomass and lipid time profile of one of the two fermentations are displayed in FIG. 3; while full process metrics from both large scale runs are listed in Table 7. On average, 180.76 g/L biomass with 126.53 g/L lipid can be produced by 200,000 L fermentor, using biodiesel crude glycerol byproduct as the only feeding carbon source, without any pretreatment or sterilization procedures. These results demonstrate the ability to use crude glycerol as a carbon feedstock for large-scale, commercial production of biomass and lipids.

TABLE 7

Large-scale (200,000 L) Fermentation Using Crude Glycerol as the only Feeding Carbon Source Without Pretreatment or Sterilization.

| | | Value | |
|---|---|---|---|
| Metrics | Units | First Batch | Second Batch |
| Fermentation time | hour | 94 | 96 |
| Final dry biomass | g/L | 172.95 | 188.56 |
| Final lipid content | % | 70.00 | 70.80 |
| Final lipid | g/L | 121.07 | 133.50 |
| Biomass productivity | g/L-d | 44.16 | 47.14 |
| Lipid productivity | g/L-d | 30.91 | 33.38 |

What is claimed is:

1. A method of producing a population of Thraustochytrid microorganisms having a selected cell density, comprising:

(a) culturing one or more Thraustochytrid microorganisms in a medium comprising crude glycerol at a first concentration level and a nitrogen source;

(b) feeding to the medium an additional amount of crude glycerol, once the first concentration of glycerol is reduced to a first threshold level of between 0 and 5 g/L, at a concentration sufficient to achieve the first concentration level, wherein a nitrogen source is not added to the medium during the feeding step;

(c) monitoring the crude glycerol concentration until the first concentration level of the crude glycerol is reduced to the first threshold level; and (d) repeating steps (b) and (c) until the selected microorganism cell density is achieved.

2. The method of claim 1, wherein the one or more Thraustochytrid microorganisms is selected from a group of genera consisting of *Thraustochytrium* and *Schizochytrium*.

3. The method of claim 1, wherein the one or more Thraustochytrid microorganisms is a *Thraustochytrium* species deposited as ATCC Accession No. PTA-6245 (ONC-T18).

4. The method of claim 1, wherein the Thraustochytrid microorganisms are capable of producing one or more fatty acids.

5. The method of claim 4, wherein the fatty acids are polyunsaturated fatty acids.

6. The method of claim 5, wherein the polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

7. The method of claim 4, wherein the method further comprises isolating the fatty acids.

8. The method of claim 1, wherein the first concentration level is between 1 and 60 g/L.

9. The method of claim 1, wherein the monitoring does not comprise measuring dissolved oxygen levels.

10. The method of claim 1, wherein the monitoring comprises obtaining a sample of the medium and determining the glycerol concentration in the sample.

11. The method of claim 10, wherein the monitoring comprises analyzing the sample using calorimetric assay, chemical reaction based calorimetric assay, fluorescence assay, HPLC assay, enzymatic assay, or combinations thereof.

12. The method of claim 1, wherein the cell density is between 50 g/L and 250 g/L.

13. The method of claim 1, wherein the microorganism cell density contains 50% to 80% by weight of total fatty acids.

14. The method of claim 13, wherein the total fatty acids comprise 10 to 45% DHA.

15. The method of claim 1, wherein the microorganism cell density contains 5 to 36% DHA by total cell weight.

16. The method of claim 1, wherein the medium comprises one or more additional carbon sources.

17. The method of claim 1, wherein the crude glycerol is not sterilized.

18. The method of claim 1, wherein the crude glycerol comprises methanol, water, ash, non-glycerin organic matter, sodium sulphate, methyl tallowate, or a combination thereof.

19. The method of claim 18, wherein the ash comprises calcium, iron, magnesium, potassium, sodium, zinc or a combination thereof.

20. The method of claim 1, wherein the crude glycerol is a biodiesel byproduct.

21. The method of claim 1, wherein the crude glycerol is not pre-treated.

22. The method of claim 1, wherein the nitrogen source comprises 4.2 g/L nitrogen.

23. The method of claim 1, wherein the desired microorganism cell density is between 160 g/L and 250 g/L.

24. The method of claim 1, wherein the nitrogen source is ammonium sulfate.

25. The method of claim 24, wherein the medium comprises 20 g/L to 25 g/L ammonium sulfate.

26. The method of claim 1, wherein the microorganism cell density contains from 70% to 80% by weight of total fatty acids.

27. The method of claim 16, wherein the one or more additional carbon source is glucose.

28. The method of claim 27, wherein the crude glycerol to glucose volume ratio is 80:20 or 20:80.

* * * * *

SEQUENCE LISTING

<160> NUMBER OF SEQ ID NOS: 1

<210> SEQ ID NO 1
<211> LENGTH: 1723
<212> TYPE: DNA
<213> ORGANISM: Artificial Sequence
<220> FEATURE:
<223> OTHER INFORMATION: Synthetic Construct

<400> SEQUENCE: 1

```
gtagtcatac gctcgtctca aagattaagc catgcatgtg taagtataag cgattatact      60
gtgagactgc gaacggctca ttatatcagt tatgatttct tcggtatttt ctttatatgg     120
atacctgcag taattctgga attaatacat gctgagaggg cccgactgtt cgggagggcc     180
gcacttatta gagttgaagc caagtaagat ggtgagtcat gataattgag cagatcgctt     240
gtttggagcg atgaatcgtt tgagtttctg ccccatcagt tgtcgacggt agtgtattgg     300
actacggtga ctataacggg tgacggggag ttagggctcg actccggaga gggagcctga     360
gagacggcta ccacatccaa ggaaggcagc aggcgcgtaa attacccaat gtggactcca     420
cgaggtagtg acgagaaata tcaatgcggg gcgcttcgcg tcttgctatt ggaatgagag     480
caatgtaaaa ccctcatcga ggatcaactg gagggcaagt ctggtgccag cagccgcggt     540
aattccagct ccagaagcgt atgctaaagt tgttgcagtt aaaaagctcg tagttgaatt     600
tctgggcgg gagccccggt ctttgcgcga ctgcgctctg tttgccgagc ggctcctctg     660
ccatcctcgc ctcttttttt agtggcgtcg ttcactgtaa ttaaagcaga gtgttccaag     720
caggtcgtat gacctggatg tttattatgg gatgatcaga tagggctcgg gtgctatttt     780
gttggtttgc acatctgagt aatgatgaat aggaacagtt gggggtattc gtatttagga     840
gctagaggtg aaattcttgg atttccgaaa gacgaactac agcgaaggca tttaccaagc     900
atgttttcat taatcaagaa cgaaagtctg gggatcgaag atgattagat accatcgtag     960
tctagaccgt aaacgatgcc gacttgcgat tgcggggtgt ttgtattgga ccctcgcagc    1020
agcacatgag aaatcaaagt ctttgggttc cgggggagt atggtcgcaa ggctgaaact    1080
taaaggaatt gacggaaggg caccaccagg agtggagcct gcggcttaat ttgactcaac    1140
acgggaaaac ttaccaggtc cagacatagg taggattgac agattgagag ctcttctttg    1200
attctatggg tggtggtgca tggccgttct tagttggtgg agtgatttgt ctggttaatt    1260
ccgttaacga acgagacctc ggcctactaa atagcggtgg gtatggcgac atacttgcgt    1320
acgcttctta gagggacatg ttcggtatac gagcaggaag ttcgaggcaa taacaggtct    1380
gtgatgccct tagatgttct gggccgcacg cgcgctacac tgatgggttc aacgggtggt    1440
catcgttgtt cgcagcgagg tgctttgccg gaaggcatgg caaatccttt caacgcccat    1500
cgtgctgggg ctagattttt gcaattatta atctccaacg aggaattcct agtaaacgca    1560
agtcatcagc ttgcattgaa tacgtccctg ccctttgtac acaccgcccg tcgcacctac    1620
cgattgaacg gtccgatgaa accatgggat gaccttttga gcgtttgttc gcagggggg    1680
tcagaactcg ggtgaatctt attgtttaga ggaaggtgaa gtc                      1723
```